(12) United States Patent
Rapkin

(10) Patent No.: US 6,502,448 B1
(45) Date of Patent: Jan. 7, 2003

(54) CHROMATOGRAPHY DETECTION SYSTEM AND METHOD

(76) Inventor: Edward Rapkin, 180 White Oak Ridge Rd., Short Hills, NJ (US) 07078

(*) Notice: Subject to any disclaimer, the term of this patent is extended or adjusted under 35 U.S.C. 154(b) by 0 days.

(21) Appl. No.: 09/391,876

(22) Filed: Sep. 7, 1999

(51) Int. Cl.$^7$ .......................... G01N 31/08; G01N 21/27; B01D 15/08; G01T 1/204

(52) U.S. Cl. ....................... 73/1.03; 73/23.41; 73/23.42; 73/864.83; 73/863.73; 210/198.2; 250/252.1; 422/89.91; 436/180

(58) Field of Search ................ 73/23.41, 23.42, 73/863.72, 863.73, 864.81, 864.83, 1.03; 95/89; 96/105; 436/180; 422/89, 91, 100; 210/659, 198.2; 250/252.1

(56) References Cited

U.S. PATENT DOCUMENTS

| | | | | |
|---|---|---|---|---|
| 3,991,626 A | * | 11/1976 | Shair ........................ | 73/23.4 |
| 4,022,577 A | * | 5/1977 | Brooker et al. ............... | 422/63 |
| 4,043,202 A | * | 8/1977 | Etheridge ................ | 73/864.83 |
| 4,271,697 A | | 6/1981 | Mowery, Jr. ............... | 73/61.52 |
| 4,446,105 A | | 5/1984 | Dinsmore et al. ........... | 422/70 |
| 4,467,038 A | * | 8/1984 | Scott ........................... | 422/89 |
| 4,699,718 A | | 10/1987 | Jones et al. ................ | 210/659 |
| 4,775,476 A | | 10/1988 | Melcher et al. ............. | 210/635 |
| 4,840,730 A | | 6/1989 | Saxena .................... | 210/198.2 |
| 4,913,821 A | | 4/1990 | Melcher et al. ............. | 210/635 |
| 5,139,681 A | | 8/1992 | Cortes et al. ............... | 210/659 |
| 5,234,599 A | | 8/1993 | Cortes et al. ............... | 210/659 |
| 5,283,036 A | * | 2/1994 | Hofmann et al. ........ | 73/864.83 |
| 5,354,662 A | * | 10/1994 | Stone et al. ................. | 436/161 |
| 5,462,660 A | | 10/1995 | Singleton et al. ........ | 210/198.2 |
| 5,492,555 A | * | 2/1996 | Strunk et al. ............... | 73/23.41 |
| 5,506,103 A | * | 4/1996 | Cohen et al. ................... | 435/6 |
| 5,559,324 A | * | 9/1996 | Rapkin et al. ........... | 250/252.1 |
| 5,591,406 A | * | 1/1997 | Hirai et al. ................. | 73/23.41 |
| 5,933,792 A | * | 8/1999 | Andersen et al. ........ | 250/252.1 |
| 6,012,487 A | * | 1/2000 | Hauck ..................... | 73/863.72 |
| 6,296,771 B1 | * | 10/2001 | Miroslav .................... | 210/143 |

* cited by examiner

*Primary Examiner*—Hezron Williams
*Assistant Examiner*—Michael Cygan
(74) *Attorney, Agent, or Firm*—Thomas L. Adams

(57) ABSTRACT

A chromatography detection system can handle the flow from a chromatography column. The chromatography detection system has an injection valve and a detector for detecting emissions from a flowing sample. The injection valve has at least one loop and is adapted to connect to the chromatography column. The valve can (a) load the at least one loop independently of the chromatography column in a first mode, and (b) serially connect the least one loop between the chromatography column and the detector in a second mode. Thus, flow from the at least one loop to the detector is driven by eluate from the chromatography column.

15 Claims, 2 Drawing Sheets

CHROMATOGRAPHY DETECTION SYSTEM AND METHOD

BACKGROUND OF THE INVENTION

1. Field of the Invention

The present invention relates to detecting emissions in eluate from a chromatography column, and in particular, to devices for incorporating test samples directly into the flow of the eluate.

2. Description of Related Art

Known emissions detectors can detect activity in the eluate from a chromatography column. These detectors allow eluate to flow through a sample cell located between a pair of photomultipliers. The eluate produces scintillations due to the interaction of radioactive components and solid scintillator located in the sample cell, or because a liquid scintillator is mixed with the eluate upstream of the sample cell. Counts thus detected can be analyzed by a computer-based system that can graphically present the counts as a function of time or as a function of energy. These known analyzers can perform various calculations with the data, and can correct the data based on various criteria.

Injector valves are commonly used in high-performance liquid chromatography (HPLC) as well as many GC systems and other analytical instruments. In HPLC, the injector valves are placed ahead of the chromatography column and serve as the means for placing a measured amount of sample into the column at a precise time. Such valves typically have a single or dual external loops. Loop volumes from perhaps 5 to 100 $\mu$L are common, but larger ones can be had. For smaller volumes a groove of suitable size is machined into the valve rotor and there is no external loop.

Multiport valves with or without sample loops have other uses. They have been used as switching valves to interchange chromatography columns while using a single pumping system. They have been used to direct the eluate exiting a column from one detector to another. They have been used to load two columns simultaneously, and to backflush one column while a second is actively used. They have been used to switch from one mobile phase to another.

Conventionally, means are provided to fill a loop while still maintaining mobile phase flow through the column. At the start of a run, a rotor in the valve is moved, which changes the porting so that mobile phase flow is now directed through the loop thereby washing its contents into the column. The valves are made to have minimum dead volumes so that sample is not lost in them and is expressed into the HPLC column without being spread out. Typically they withstand pressures of several thousand psi.

In the past, to check the efficiency of the radioactive detection process, the typical user collects eluate in a vial from a chromatography column at a peak by watching for the peak on a monitor screen, which is providing measurement data from a flow-through detector, a continuous detector of radioactivity connected to the output of the column. The user then takes this vial to a liquid scintillation sample counter and measures it. The peak may or may not be well-defined depending upon the chromatography. Collecting a sample in this fashion will only produce small volumes: just the peak volume of the mobile phase if using solid scintillator, or the mobile phase plus 3–4 additional volumes with liquid scintillator. Most static sample counters require much larger volumes, so the user must dilute the sample with scintillator solution thereby changing the performance from what it was in the flow-through detector. Then, since the user is counting an unknown, that sample is calibrated by addition of an internal standard of known activity and recounting. The overall result is not very accurate. Finally the calibration must be brought back to the original system and entered into the associated software.

Double isotope counting is avoided by many who do not appreciate the mathematics of correcting for spectral overlap in HPLC. One simplification many people make is to spend a great deal of time adjusting their counting windows so that they only look at that portion of the more energetic isotope that lies completely above the most energetic events of the less energetic isotope. Doing that can lose significant counting efficiency, e.g. for $^3H/^{14}C$ dual-label counting, to eliminate the last 1% of $^3H$ in the $^{14}C$ channel might result in a 10% reduction in $^{14}C$ counts. If users had a simple way to obtain measurements of the spectral distribution of the different isotopes, they might be more inclined to use such measurement data to calculate corrections for such overlap or spillover.

Variable quench correction is not widely practiced, and then only with liquid scintillator, not with solid (though there is some belief that it should be). First, the sample concentration in an HPLC eluate stream is extremely low; quenching, if any, primarily comes from the composition of the mobile phase itself and variable quenching occurs because the mobile phase is deliberately changed during a run to push different compounds off the column. The normal terminology is "gradient elution" and the gradients often are of different salts and buffers, or water and miscible organic solvents.

Quench correction is not normally practiced for several reasons. Users hope that they will not need the correction, and, because the method seems complex, they do not try to learn whether they really do need this correction. Further, the correction when practiced in the conventional manner, may offer the promise of accuracy, but will require that substantial isotope be consumed, which also discourages frequent repetition.

The method commonly recommended by manufacturers of flow-through detectors—which is only applicable to liquid scintillation counting—is to make a dummy run with no sample, but otherwise identical in every aspect to the anticipated sample runs. Radioactive standard is added to the scintillator solution prior to the dummy run. The run is made and the activity is counted throughout. Since activity level of the scintillator is known, as well as its flow rate, one can create a table—from data collected minute by minute—of performance vs. time. When the sample runs are later made, measurements are corrected minute-by-minute using the above performance table.

The problem with this technique is that very large quantities of standard are required. If the chromatography run lasts one-hour with scintillator flowing at 3 ml/min through a 1 ml cell, and one needs to count at 10,000 counts per minute to obtain good statistics and the counting efficiency is about 50% (if it was much higher no one would worry about quenching), the total activity needed is about 3,600,000 disintegrations per minute. That activity is fairly high for a calibrated standard; it does not pre-suppose that this would be done often, yet it is necessary after any change in the analytical procedure: run length, gradient composition, gradient change rate, counting windows, counting cell size, etc.

Percent recovery is also of interest to many users (that is, determining how much of the activity that went into the HPLC column was actually measured in the flow-through detector.) Sometimes activity stays on the HPLC resin, and sometimes it sticks to the stainless steel or plastic tubing. A convenient measurement technique does not currently exist. The operator might pipette a known volume of the original sample mixture into a liquid scintillation vial and count it in a static sample counter. Then the operator must apply all the corrections mentioned above to translate that result to what the flow-through detector gives. It would be better if the raw sample prior to chromatographic separation could be counted in the flow-through detector and each peak subsequently separated is reported as a percent of that sample.

In FIG. 1 of U.S. Pat. No. 4,775,476 eluent passes through 10-port valve 20 to pickup sample through tubular membrane 35. Thereafter, the sample and eluent are directed by the valve through sample loop 27 before arriving at detector 34. In FIG. 2 valve 20 is switched so that eluent is pumped through sample loop 27 to the chromatography column 30, whose eluate is supplied to the detector 34. In this system a sample is not loaded downstream of the chromatography column. Instead, the column is either supplied from the sample loop, or is bypassed while the detector is fed through the sample loop.

In U.S. Pat. No. 4,271,697 sample valve 24 can supply a sample through valve 33 to chromatography column 46, whose eluate is delivered through valve 33 to detector 51. Valve 33 can be switched to backflush column 46 into sample loop 92, associated with valve 34. Loop 92 can supply sample to a second chromatography column 99, whose eluate can be delivered through valve 33 to detector 51. This sample loop is actually between two columns and is therefore unable to directly supply a detector.

U.S. Pat. Nos. 4,840,730; 4,913,821; 4,699,718; and 5,462,660 show sample loops, but these loops are positioned upstream of a chromatography column, in the conventional manner. U.S. Pat. Nos. 5,139,681 and 5,234,599 do not disclose a sample loop, except for an irrelevant mention of a sample loop at column 5, line 63. See also U.S. Pat. No. 4,446,105 (no sample loop).

Accordingly, there is a need for an effective system and method that will allow these, and other useful tests to be outlined herein, to be performed conveniently, so operators will be encouraged to perform them more regularly.

SUMMARY OF THE INVENTION

In accordance with the illustrative embodiments demonstrating features and advantages of the present invention, there is provided a chromatography detection system for handling the flow from a chromatography column. The chromatography detection system has an injection valve and a detector for detecting emissions from a flowing sample. The injection valve has at least one loop and is adapted to connect to the chromatography column. The valve is operable to (a) load the at least one loop independently of the chromatography column in a first mode, and (b) serially connect the at least one loop between the chromatography column and the detector in a second mode.

According to another aspect of the invention a method is provided, employing at least one loop and an emissions detector, for handling the flow from a chromatography column. The method includes the step of loading the at least one loop independently of the chromatography column in a first mode. The method also includes the step of serially connecting the at least one loop between the chromatography column and the detector in a second mode. Thus, flow from the at least one loop to the detector is driven by eluate from the chromatography column.

By employing systems and methods of the foregoing type, various tests can be conveniently performed. In one preferred embodiment, a ten port injection valve has one port connected to the outlet of a chromatography column, and another port connected to the inlet of an emissions detector. In some embodiments, the emissions detector can have a T-fitting to introduce a scintillator solution before sending the sample to a sample chamber in a radiochromatography detector, which employs a pair of photomultiplier tubes. Alternatively, the detector can have a solid scintillator in the sample chamber, thereby eliminating the scintillator solution and T-fitting.

Two pairs of ports on the injection valve can connect to two separate loops. Four other ports can be used to fill and drain the two loops. The system is arranged so that with the valve in a first position, one loop is serially connected between the chromatography column and the detector, while the other loop can be filled independently of the chromatography column. When the valve is in a second position, the function of the two loops is essentially interchanged. This arrangement allows an operator to fill each loop with the same or with different solutions. By carefully loading these two loops and by switching them into play at the appropriate time, a variety of tests can be conveniently performed.

An injection from a loop may be done for a sample that might be measured in entirety without chromatographic separation. Alternatively, a standardized quantity of radioactive isotope can be injected directly into the detector for various purposes such as: (1) providing a scale for subsequent measurements from the chromatography column; (2) sending a standard through the detector to either precisely measure efficiency or simply to observe any general trends indicating a change in efficiency; (3) more sophisticated tests that sequentially inject different isotopes or different eluates to enable correction for more subtle phenomenon (spillover and quenching).

For isocratic operation or for gradient runs where the efficiency does not change significantly (which is most often the case), two loops enable determination of single- or dual-isotope efficiency, as well as spillover for dual-isotope counting. For quench correction, dual isotope correction could be facilitated, although this is an infrequent requirement.

In a simple embodiment, the user will manually fill the loop and then control the injection with a handle or a pushbutton. Other embodiments can automate the filling and can rely on programmed actuation.

By using an injector valve with separate loops, one can conveniently determine efficiency by loading into a loop, the same internal standard as would be used to check a vial of eluate at a separate liquid scintillation sample counter, as described previously. The result should be equivalent to that obtained when measuring an unknown. Here however, the counting can be advantageously performed with the same instrument, with the mobile phase being the same, and with the scintillator (solid or liquid) being the same. Then, once the process is over, the result can be manually or automatically incorporated into any software used for correction of that run and all subsequent runs, until a new standard injection is made.

Systems of the foregoing type can be used to evaluate the effect of spillover in dual-isotope chromatography. For example, chromatography can be performed with samples containing a mixture of isotopes, often $^3H$ and $^{14}C$. By using the injection valve with one loop filled with a $^3H$ standard and the other filled with a $^{14}C$ standard one can be much less exacting with the window settings for the energy spectrum. (Actually, in a practical plumbing arrangement, where the mobile phase must continue to flow before the actual run starts, the second loop will start as a bypass and will typically be filled after the first one is drained.) When the first loop is drained, the operator can determine how much $^3H$ falls in each channel. Then, when the second loop is drained, the operator can determine how much $^{14}C$ is in each channel. With that information, preferably a computer will perform the proper mathematics and automatically incorporate the results into subsequent runs.

Also, with arrangements of the foregoing type, one can evaluate efficiency in spite of gradient elution. It is possible to make periodic injections during a dummy run, record the performance, and then use interpolation between the points. A few intermittent injections may not be quite as comprehensive as making measurements across the entire run, but such thoroughness may be unnecessary. One would expect the most popular usage to be "before and after" injections to verify that there has not been significant quenching. Even such sparse measurements are an improvement over the conventional situation, where checks are difficult and extremely rare, and the unverified assumption is made that nothing has changed during the run. Also, using the above injection valve will allow checking the performance of packed cells during gradient elution, something not being done by any means at this time.

An operator can also determine percent recovery with the preferred injection valve. When a run starts, before the first peak appears (almost always there is a delay of several minutes) the combined sample can be pushed out of the loop through the detector and the total count recorded. It is then a simple matter to report each peak as a percent of that total. Because a typical loop may be 20 µL while the amount of sample in the run is 50 µL, or some other amount, one must make provision for a normalization factor, but essentially that is all.

In practice, the preferred injection valve provides a quick response. Typically, within a few seconds of the valve actuation, there are sharp, well-defined peaks. If any of these standards/samples entered the detector via an HPLC column instead of from the downstream loop, there would be a delay of minutes to sometimes an hour or more until a peak appeared. Moreover, chromatography tends to spread peaks and flatten them or sometimes make them overlap, which is why one would not want to involve the HPLC system in any of these measurements, even if it were possible.

In these situations (efficiency, quench correction, etc.) the preferred plumbing arrangement allows one or both loops to always be connected to a reservoir of standard activity. If only one isotope is used, one loop merely serves as a bypass. If both single-isotope efficiency calibration, and single-isotope quench correction are practiced, the same standard solution will serve for both. The quantity of standard solution required is remarkably little. With 10 µL loops, and with wastage being four times the loop volume, 10 mL of standard solution will enable 200 calibrations (which may be more than are now performed over the life of many instruments).

It is considered simplest and best that both efficiency and quench calibrations be performed in dummy runs which precede runs of unknown samples. Efficiency runs need only last for short periods, a few minutes at most, but quench calibration runs must mimic the anticipated sample runs as to time and gradient.

BRIEF DESCRIPTION OF THE DRAWINGS

The above brief description as well as other objects, features and advantages of the present invention will be more fully appreciated by reference to the following detailed description of presently preferred but nonetheless illustrative embodiments in accordance with the present invention when taken in conjunction with the accompanying drawings, wherein.

DETAILED DESCRIPTION OF THE PREFERRED EMBODIMENTS

Figure 2:
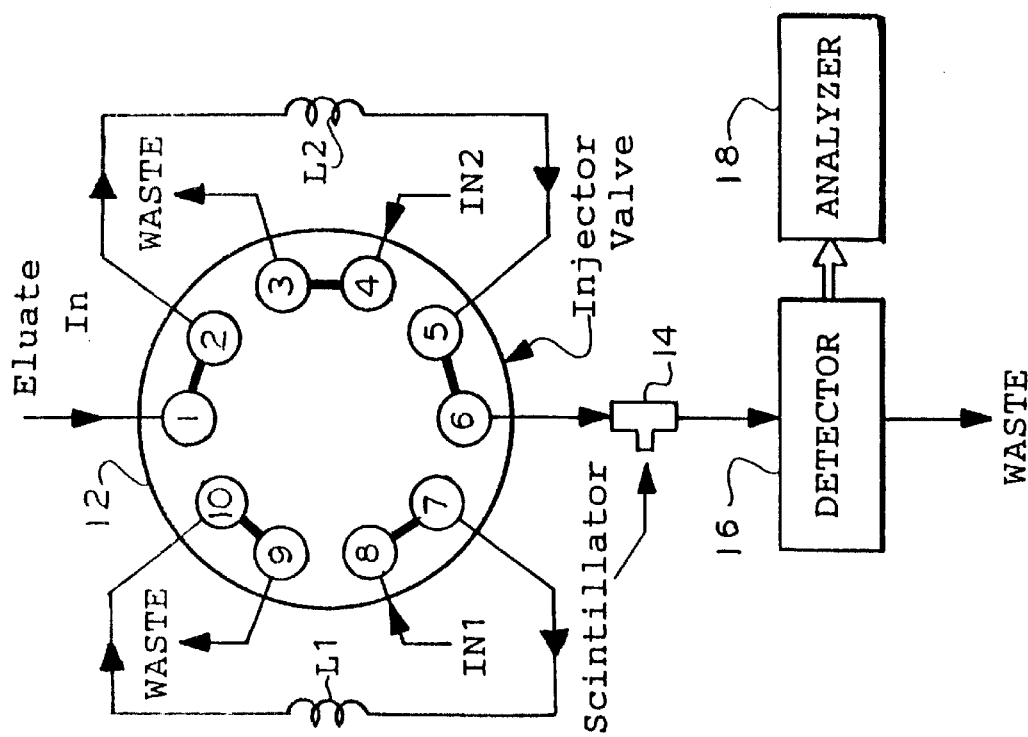
FIG. 2 is a schematic diagram of the system of FIG. 1 in a second mode.
Figure 1:
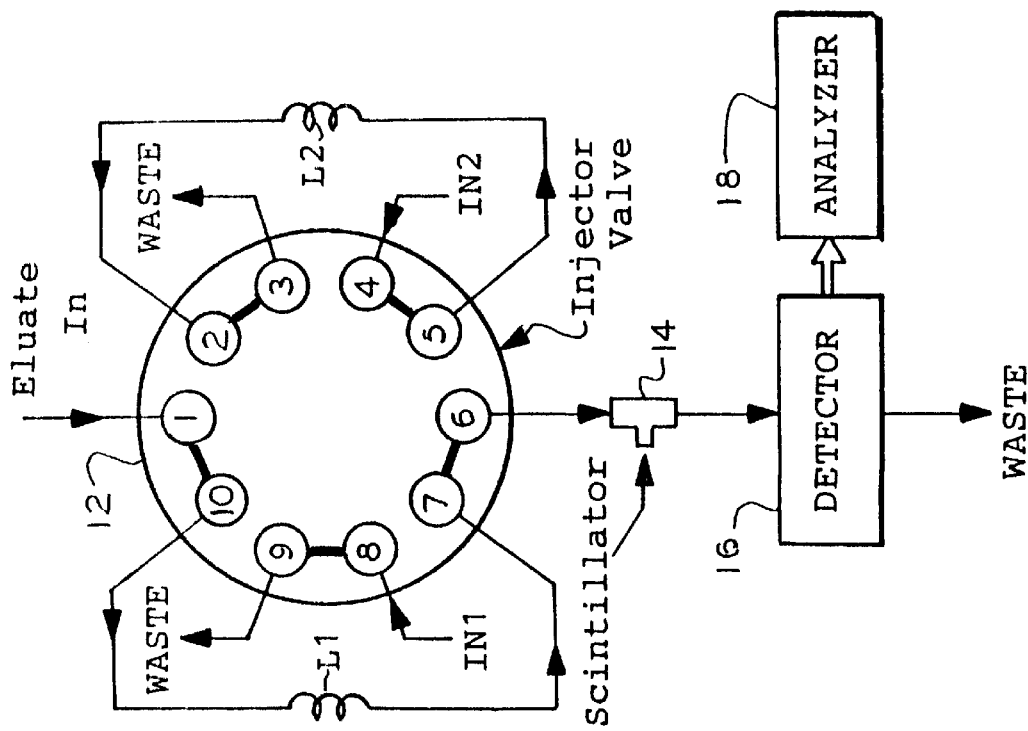
FIG. 1 is a schematic diagram of a chromatography detection system in a first mode for performing a chromatography detection method.

Referring to FIGS. 1 and 2, a chromatography detection system is shown with an injection valve 12 having ten ports 1–10. Valve 12 is shown in a first mode in FIG. 1, where the ports are connected as follows: 1–10; 2–3; 4–5; 6–7; 8–9. A second mode is shown in FIG. 2 with the ports connected as follows: 1–2; 3–4; 5–6; 7–8; 9–10. Valves of this type can be obtained from such suppliers as Rheodyne and Valco. Such valves are offered with the ability to handle relatively high pressures, for example, 5000 psi ratings. High-pressure ratings are required primarily for operation with the solid scintillators described further hereinafter (as opposed to liquid scintillators). Such valves typically have a single or dual external loops.

The illustrated valve 12 has an external loop L1 connected between ports 7 and 10, and an external loop L2 connected between ports 2 and 5. Typically, loops L1 and L2 will have a volume of 10 or 20 µL, although other volumes are anticipated. For smaller volumes, a different type of injection valve can be used with one or more grooves of suitable size machined into the valve rotor to eliminate the need for external loops.

Ports 4 and 8 can be arranged with needle ports IN1 and IN2 (either built-in or external) for injecting a sample, a standard, or the like. In the other embodiments, ports 4 and 8 may be connected through an appropriate pumping device to a reservoir. Ports 3 and 9 are connected to drain to waste. Port 1 connects to the outlet of a chromatography column (not shown in these figures). Port 6 connects to one inlet of a T-connector 14, whose other inlet is connected to a source of liquid scintillator. Accordingly, connector 14 can act as a means for adding scintillator.

The outlet of connector 14 connects to a flow-through detector 16, whose outlet drains to waste. Detector 16 may be of the type shown in U.S. Pat. No. 5,559,324, although other embodiments may use a simpler detector without a built-in, standard source of radiation. In a simple form, detector 16 contains a sample cell that allows a sample to flow between a pair of photomultiplier tubes, which detect radiation-induced scintillation produced by a solid scintillator in the sample cell, or by a scintillator fluid mixed with the sample. In instances where detector 16 contains a solid scintillator, connector 14 is unnecessary (or the flow of scintillator fluid into connector 14 may be terminated).

The output of detector 16 can be delivered to an analyzer 18. Analyzers of this type can record and display the counts detected by detector 16, and can include various features for labeling peaks, analyzing the area under the peaks, distinguishing energy levels, correcting the measurements according to a variety of criteria, etc. These analyzers typically include a micro-computer for performing such analysis. Such analyzers are available from IN/US SYSTEMS, INC., Pine Brook, N.J., as part of a β-RAM™ system.

Injection valve 12 can be switched between the two modes shown in FIGS. 1 and 2 by manually operating a lever on the valve, although in preferred embodiments the valve switching will be performed by a motor, solenoid or other actuator controlled by a pushbutton (not shown). In more advanced embodiments, analyzer 18 will have an output that is programmed to directly control the foregoing actuator upon a predetermined event or at a pre-programmed time.

In the mode of FIG. 1, loop L2 can be loaded by injecting a standard or sample through needle port IN2. At the same time, eluate from the chromatography column can flow through ports 1 and 10 into loop L1, and then through ports 7 and 6 to the connector 14. In the mode of FIG. 2, loop L1 can be loaded by injecting a standard or sample through needle port IN1. At the same time, eluate from the chromatography column can flow through ports 1 and 2 into loop L2, and then through ports 5 and 6 to the connector 14.

Figure 3:
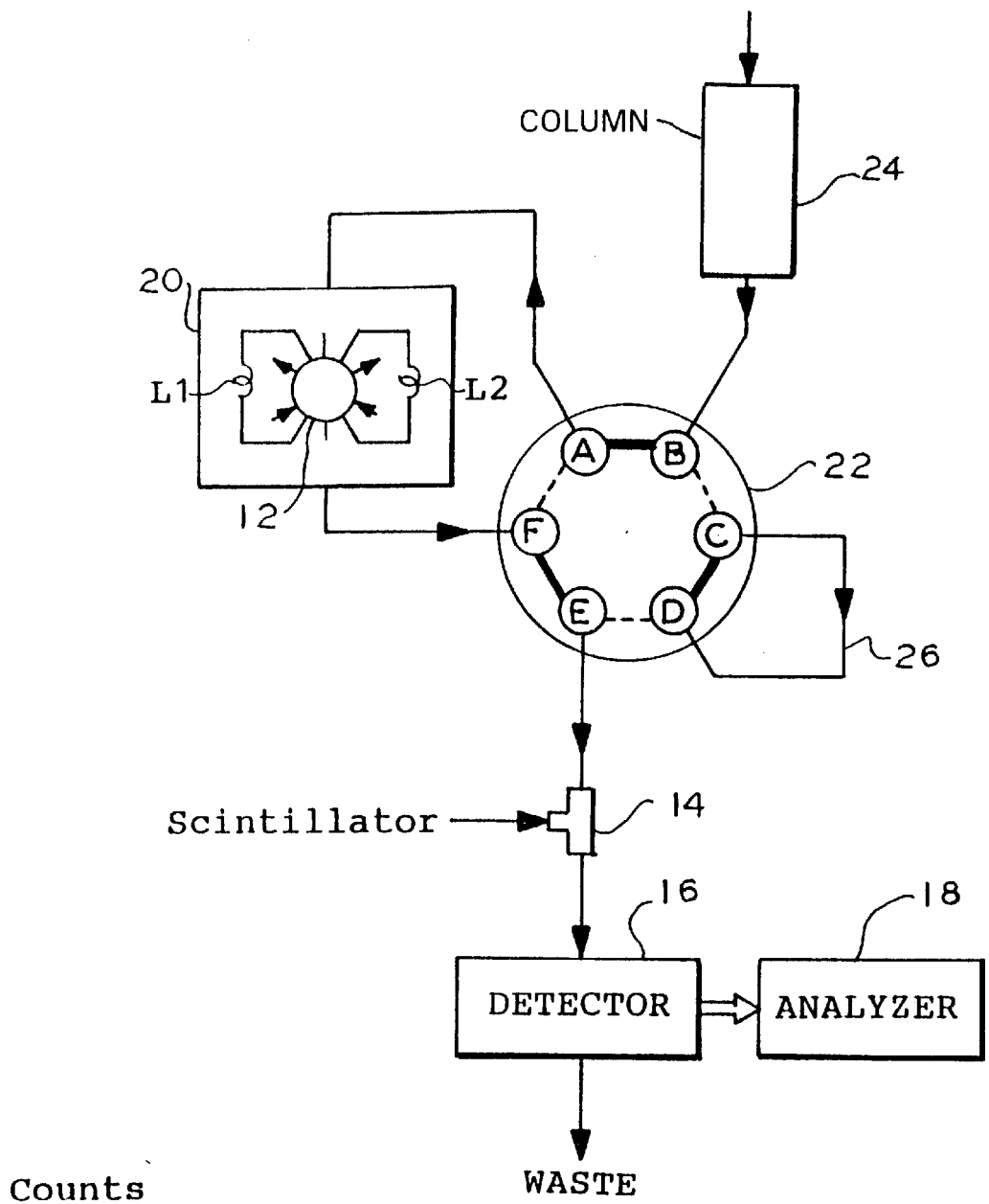
FIG. 3 is a schematic diagram illustrating a modified version of the system of FIGS. 1 and 2.

Referring to FIG. 3, subsystem 20 contains previously mentioned injection valve 12, connected as before with loops L1 and L2. In this embodiment, previously mentioned port 1 of valve 12 is connected to port A of valve 22. Port 6 of valve 12 is connected to port F of valve 22. The outlet of chromatography column 24 connects to port B of valve 22, while ports C and D are connected together by line 26. Port E connects to an inlet of previously mentioned connector 14, which is connected as before to a source of scintillator fluid and to detector 16.

Valve 22 is shown with the following ports connected together: A–B; C–D; E–F. In this condition, the outlet of chromatography column 24 connects directly to port 1 of valve 12, while port 6 of valve 12 connects to an inlet of connector 14. Accordingly, this condition is identical to that described in FIGS. 1 and 2. The broken lines of valve 22 indicate the alternate state of valve 22, where the following ports connect together: B–C; D–E; F–A. In this latter condition, chromatography column 24 connects through line 26 to an inlet of connector 14, thereby bypassing block 20. Accordingly, this latter condition is a conventional configuration, effectively eliminating block 20.

To facilitate an understanding of the principles associated with the foregoing apparatus, its operation will be briefly described. Operation will be described in connection with the arrangement of FIGS. 1 and 2. The embodiment of FIG. 3 provides an alternative when it might be desirable to completely bypass the two sample loops of valve 12, thereby allowing both of them to be filled with test sample at the same time.

In the mode illustrated in FIG. 1, eluate from the chromatography column can flow through ports 1 and 10 through loop L1 into T-connector 14. Loop L1 may be initially empty, so that the eluate is mixed with scintillator fluid at connector 14 to arrive at detector 16, in the conventional manner. At this time, the operator may inject into port 4 a sample or standard that fills loop L2, the excess being drained from port 3 to waste.

When valve 12 is switched to the mode shown in FIG. 2, loop L2 is connected in series between the outlet of the chromatography column and the inlet of connector 14, so that the substance previously loaded into loop L2 will immediately flow through connector 14 into detector 16. This subsequent flow through loop L2 will be the reverse of the flow that occurred when the loop was being filled. While loop L2 is feeding the detector, an operator can inject into port 8 a sample or standard that fills loop L1, the excess being drained from port 9 to waste. Accordingly, if the valve 12 is switched back to the mode shown in FIG. 1, loop L1 is then connected in series between the outlet of the chromatography column and the inlet of connector 14, so that the substance previously loaded into loop L1 will immediately flow through connector 14 into detector 16.

Procedures of this type can be performed to determine efficiency. When efficiency calibration is desired, the operator will record whether the run is for single- or dual-isotope counting and also the number of dpm (disintegrations per minute) to be put in the loop(s). (In some cases, this data will be stored in analyzer 18.) For either single- or dual-isotope measurement, the injection loop that is not on-stream (for example, loop L2 of FIG. 1) is filled with a first standard. (It is the only standard employed for single-isotope work, but is the lower energy isotope for dual-isotope counting.) A dummy or an actual run is begun by pumping fluid through the chromatography column. Once some baseline is established, the injection valve 12 is actuated (changing from the mode of FIG. 1 to that of FIG. 2) and the first standard will be washed into the flow-through detector 16 and be completely counted in short order, depending upon flow rates and cell volumes.

Assuming this is a single-isotope efficiency check, this known amount of activity of the isotope in question is passed from the loop L2 through the detector 16 just after the start of a run. The peak is integrated by analyzer 18, and the efficiency calculated manually or automatically, which efficiency calculation can be applied to all later peaks.

If however, the counting of a second isotope is needed, the second loop L1 is filled while the other one is emptying. There is no time pressure. Filling may be done immediately or leisurely. Once the run is back to baseline from the first peak, the valve 12 is again actuated and the second isotope is measured. Operation is continued until baseline is again achieved, at which point the run may be terminated if a dummy run, or continued if an actual run.

Thus, there will be one or more peaks associated with the loops. Peaks are easily selected manually or automatically; experience shows that when activity in a small bolus is directly injected into the flow-through detector, peaks are sharp and well-formed. With sufficient activity in the standard (10,000–100,000 dpm) background need not be considered and counting statistics are quite good. With the activity and the flow parameters known, counting efficiencies and spillover are readily calculated and reported. They may then be automatically inserted into the operating parameters for subsequent counting, overriding whatever parameters may have been placed there previously.

In each instance, it is desirable to label the peak in some fashion, perhaps by name, e.g. STD 1, STD 2, Q 1, Q 2, etc., which probably is best done manually—the standard run is always the first in a series and the operator can arrange to be there. Once that special notation is made, the operator can record the activity in the injection loop, and only the results of those peaks receive the special mathematical treatment. They do not become part of the grand totals of an actual run. Any analysis shows them to be something special and distinct.

These injected peaks will be well-defined as the activity is not subjected to chromatography; there should be neither significant spreading nor tailing. Moreover, in contrast to samples which users may take to liquid scintillation counters, they are counted in exactly the same way as are all the other peaks derived from subsequent chromatography—the same scintillator (liquid or solid), the same photomultipliers, the same background, the same optics, etc.

The operator may also wish to evaluate the percent recovery of the sample that will be separated by the chromatography column. In this instance, one of the loops L1 or L2 will be filled with that sample. The operation will be as before, except that the initial peak will be a composite of all of the peaks that will eventually come from the chromatography column. Accordingly, the operator can value these subsequent peaks as a percentage of the initial composite peak.

Figure 4:
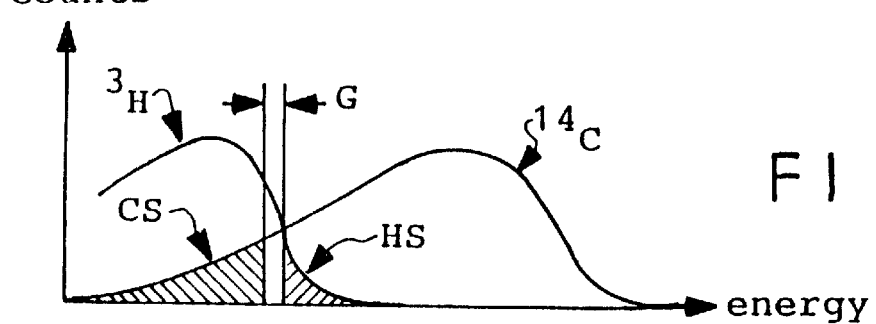
FIG. 4 shows the overlapping energy spectrum for dual-isotopes.

To evaluate spillover from dual-isotope operation, the loops L1 and L2 are filled with the two different isotopes. FIG. 4 shows the overlapping count density for two isotopes ($^3H$ and $^{14}C$) as a function of energy. During an actual run, these isotopes will have distinct peaks at different energy levels. To distinguish between the two isotopes, the analyzing equipment will be set with two different energy windows, above and below the energy gap G. Counts above the energy gap G originate primarily from disintegrations of $^{14}C$, but include some counts HS associated with spillover of the upper part of the $^3H$ spectrum into the counting window primarily intended for $^{14}C$. Counts below the energy gap G originate primarily from disintegrations of $^3H$, but include some counts CS associated with spillover of the lower part of the $^{14}C$ spectrum into the counting window primarily intended for $^3H$.

When the two loops L1 and L2 contain separate samples of the different isotopes, they can be injected at different times so that their distribution between the two energy windows can be separately analyzed without interference from the other isotope. Accordingly, the counts associated with the spillover segments CS and HS can be separately measured and then used as corrections during the actual run.

It is expected that variable quenching, is usually due to gradient change. To make this evaluation, the same known amount of activity is injected at the beginning and end of the gradient from one or both of the loops L1 and L2 (again, possibly a dummy run). Retention times and efficiencies are determined and interpolation is applied across this run and subsequent runs. The ease of performing this technique will encourage its frequent use, with more accurate techniques being reserved only for instances where such accuracy is truly needed. Often, an operator need not have highly accurate results, but may only need to know if there is a trend of diminishing accuracy.

In some embodiments where the computer resources are available, an operator might make several injections at different times during a standardization run, rather than just before and after. There can then be interpolation between adjacent points. One would either have to know in advance something about the run to prevent injecting standard on top of a sample peak; or better yet, make these multiple injections during a dummy run.

When injecting during a dummy run, the operator can precisely parallel the intended sample runs as to gradient and time. It is assumed that quench correction will most often be practiced for single-isotope counting, though with the preferred equipment, the proposed method could be extended to dual isotope work.

Prior to such a run, the operator will record the number of dpm in each injection. The operator may then make as many injections during the dummy run as deemed advantageous. Once the run has ended, peaks are marked, the efficiencies along the way are calculated, the times of the peaks are noted, and a table of time vs. efficiency is established. When the samples are next run, that table is employed with interpolation between points.

In dual isotope counting and single isotope quench correction (possibly even with single isotope efficiency checks), knowing the number of dpm injected may be unnecessary. When the operator is called upon to record dpm, if the number of cpm (counts per minute) observed were to be recorded, the final results would be in cpm corrected back to the standards.

The foregoing methods offer simplicity over current practice. Primarily, the convenience of use encourages the operator to check performance, something not done with sufficient frequency and often done rather poorly. When working with gradients, the present technique should particularly encourage routine "before and after" efficiency determinations, which, if not too dissimilar, would give support in particular cases to the notion that quench correction is not needed. However, if correction is needed, at least two-point correction will be performed and will be better than no-point correction (while the convenience of the present technique makes multiple point corrections more likely).

The preferred technique eliminates pipetting errors and the problems of incompletely thawing frozen standards. Moreover, numerous other difficulties are avoided: Determining efficiency by employing a liquid scintillation counter located at some distance with unknown settings; measuring a sample in a solution not used in the flow-through detector; not knowing whether all of the sample actually went through the detector; not using the same sample over lengthy periods possibly extending over years, yet expecting the same results, etc. Unfortunately, all these difficulties are more common than is the making of proper measurement. Even with good measurements, operators often do not understand dual-isotope computations well enough to do them correctly. The preferred method ameliorates all these failings.

It is appreciated that various modifications may be implemented with respect to the above described, preferred embodiments. While a 10 port is disclosed, other embodiments may use one or more valves having a different number of ports, depending upon the number of loops, the desired plumbing arrangements, simplicity, etc. Also, the volume and number of loops can be altered depending upon the system requirements. Also, a variety of detectors and sample cells can be employed, depending upon the type and volume of the expected emissions. In addition, analyzers of various types can be employed and in some embodiments analysis will be performed without employing computers, with calculations being done manually. Moreover, chromatography of various types can be employed, including gas, liquid, low pressure, etc. Furthermore, the foregoing methods can be altered by including additional steps, deleting some steps, rearranging some steps etc. Also, a variety of methods were disclosed for evaluating different phenomena (efficiency, spillover, gradient elution, etc.) and one or more of these methods may be combined in a single run with the various steps taken in various sequences.

Obviously, many modifications and variations of the present invention are possible in light of the above teachings. It is therefore to be understood that within the scope of the appended claims, the invention may be practiced otherwise than as specifically described.

What is claimed is:

1. A chromatography detection method employing an injection valve with at least one loop and a flow-through emissions detector, for handling the flow from a chromatography column, comprising the steps of:

loading said at least one loop with an independent sample having a known activity and including a standard quantity of an isotope diluted with mobile phase as employed in said chromatography column, said independent sample being derived from an independent source independently of said chromatography column in a first mode without connecting said at least one loop to either said flow-through detector or said chromatography column;

serially connecting said at least one loop between said chromatography column and said flow-through emissions detector in a second mode for unloading said independent sample;

causing said independent sample to flow by driving a flow from said at least one loop to said detector with eluate from said chromatography column;

detecting emissions in said second mode as said independent sample flows through said flow-through emissions detector;

determining efficiency of said emissions detector by calculating the efficiency of detected emissions with respect to the known activity of said independent sample based on the flow of said independent sample through said emissions detector;

detecting emissions when said independent sample is absent from said emissions detector and eluate from said chromatography column is present in said emissions detector; and correcting emissions readings for flow from said chromatography column using the efficiency determined from the flow of said independent sample through said emissions detector.

2. A chromatography detection method according to claim 1 wherein said step of loading is performed by injecting into said at least one loop a standard sample having a predetermined emissions rate, the step of serially connecting said at least one loop in said second mode being followed by the step of:

calibrating said emissions detector based upon said standard sample after it has flowed through said detector.

3. A chromatography detection method according to claim 1 wherein said step of loading is performed by injecting into said at least one loop a bolus corresponding to the sample being fed to said chromatography column, the step of serially connecting said at least one loop in said second mode being followed by the step of:

measuring the response of said emissions detector as said bolus flows through said detector in order to get a non-fractionated measurement base against which eluate from said chromatography column is compared.

4. A chromatography detection method according to claim 1 wherein said step of loading is performed by injecting into said at least one loop an independent sample, the step of serially connecting said at least one loop in said second mode being followed by the step of:

measuring the response of said emissions detector as said independent sample flows through said detector in order to evaluate emissions of said independent sample without chromatographic separation.

5. A chromatography detection method according to claim 1 wherein said step of loading is performed by injecting into said at least one loop a test sample including a standard quantity of an isotope diluted with eluant as employed in said chromatography column, the step of serially connecting said at least one loop in said second mode being followed by the step of:

measuring the response of said emissions detector as said test sample flows through said detector, to evaluate the effect of eluant on counting efficiency.

6. A chromatography detection method system according to claim 1 comprising the step of:

draining said at least one loop to waste in said first mode.

7. A chromatography detection method according to claim 1 comprising the step of:

adding scintillator fluid upstream of said detector.

8. A chromatography detection method employing an injection valve with one or more loops and a flow-through emissions detector, for handling the flow from a chromatography column, wherein said chromatography column receives samples having a distinct pair of isotopes, comprising the steps of:

loading said one or more loops with a first independent sample derived from an independent source derived independently of said chromatography column, said first independent sample including a standard quantity of one of said distinct pair of isotopes having a known activity and being diluted with mobile phase as employed in said chromatography column;

loading into said one or more loops, at a different time, a second independent sample having a known activity and including a standard quantity of a different one of said distinct pair of isotopes diluted with mobile phase as employed in said chromatography column, said first and said second independent sample being derived independently of said chromatography column without connecting said one or more loops to said chromatography column;

serially connecting said one or more loops repeatedly between said chromatography column and said flow-through emissions detector in order to unload said first and said second independent sample at different times;

measuring the energy distribution indicated by said emissions detector as different ones of said isotopes from said first and said second independent sample flow through said detector, noting the fractions above and below a predetermined energy gap; and correcting measurements by said emissions detector of eluate from said chromatography column based on the extent of overlapping of energy distributions for said pair of isotopes relative to said predetermined energy in order to correct for spillover effects in eluate from said chromatography column.

9. A chromatography detection method according to claim 1 wherein said chromatography column receives at least two separately variable eluants, and wherein said step of loading is performed repeatedly by repeatedly injecting a predetermined isotope with different eluants into said at least one loop at separate times corresponding to elution with variable ones of said eluants, the step of serially connecting said pair of loops is performed repeatedly and includes the step of:

measuring the response of said emissions detector as said isotope repeatedly flows through said detector, so that the effect of gradient elution can be evaluated and used to correct for quenching or other inefficiencies.

10. A chromatography detection method according to claim 1 wherein another loop is provided as a complement to said at least one loop to comprise a pair of loops, and wherein the step of loading said at least one loop comprises:

loading a first and a second one of the pair of loops independently of said chromatography column in said first-and said second modes, respectively, the step of serially connecting said at least one loop comprises:

serially connecting, between said chromatography column and said detector, (a) the first one of said loops in said second mode, and (b) the second one of said loops in said first mode, said first and second modes occurring in separate time intervals.

11. A chromatography detection method according to claim 10 wherein said chromatography column receives samples having a distinct pair of isotopes, and wherein said step of loading is performed by injecting into different corresponding ones of said pair of loops, different ones of said distinct pair of isotopes, the step of serially connecting said pair of loops in said first and said second mode including the steps of:

measuring the energy distribution indicated by said emissions detector as different ones of said isotopes flow through said detector in said first and said second modes, so that the extent of overlapping of energy distributions for said pair of isotopes can be evaluated and used to correct for spillover effects in eluate from said chromatography column.

12. A chromatography detection method employing one or more loops and a flow-through emissions detector, for handling the flow from a chromatography column, wherein said chromatography column receives at least two, different eluants in time varying proportions, comprising the steps of:

loading into said one or more loops a first independent sample derived from an independent source independently of said chromatography column and having a predetermined isotope with a first one of said two different eluants;

loading into said one or more loops a second independent sample having said predetermined isotope with a second one of said two different eluants, said first and said second independent sample being derived independently of said chromatography column without connecting said one or more loops to said chromatography column;

serially connecting said one or more loops between said chromatography column and said flow-through emissions detector in order to unload said first and said second independent sample at different times;

measuring the response of said emissions detector to said first and said second independent sample as said isotope flows through said detector at separate times to produce separate values corresponding to elution with different compositions of said eluants; and correcting measurements by said emissions detector of eluate from said chromatography column that was mixed with said different eluant compositions by using different corresponding ones of said separate values, so that the effect of gradient elution can be evaluated and used to correct for inefficiencies such as quenching.

13. A chromatography detection method according to claim 10 wherein each of said pair of loops, when connected to said chromatography column, are connected downstream from said chromatography column.

14. A chromatography detection method according to claim 13 said first one and said second one of said pair of loops drain to waste in said first and said second modes, respectively.

15. A chromatography detection method according to claim 13 comprising the step of:

adding scintillator fluid upstream of said detector.

* * * * *